(12) United States Patent
Coleman et al.

(10) Patent No.: US 8,796,446 B2
(45) Date of Patent: Aug. 5, 2014

(54) EXTRACTION OF CARBOXYLIC ACIDS WITH TIN COMPOUNDS

(75) Inventors: David T. Coleman, Daphne, AL (US); Edward Micinski, Martinez, GA (US); James Edwin Wiley, Jr., Moraga, GA (US); Thomas A. Eilers, Singapore (SG); David A. Dentel, Singapore (SG)

(73) Assignee: Tate & Lyle Technology Limited, London (GB)

( * ) Notice: Subject to any disclaimer, the term of this patent is extended or adjusted under 35 U.S.C. 154(b) by 0 days.

(21) Appl. No.: 13/463,332

(22) Filed: May 3, 2012

(65) Prior Publication Data

US 2012/0289693 A1 Nov. 15, 2012

Related U.S. Application Data

(60) Provisional application No. 61/484,476, filed on May 10, 2011.

(51) Int. Cl.
C07H 1/06 (2006.01)
C07H 1/00 (2006.01)
C07C 231/24 (2006.01)

(52) U.S. Cl.
USPC .......................... 536/119; 536/122; 564/216

(58) Field of Classification Search
USPC .................................. 536/119, 122; 564/216
See application file for complete search history.

(56) References Cited

U.S. PATENT DOCUMENTS

| | | | |
|---|---|---|---|
| 4,783,526 A | 11/1988 | O'Brien | |
| 4,889,928 A | 12/1989 | Simpson | |
| 4,950,746 A | 8/1990 | Navia | |
| 4,980,463 A | 12/1990 | Walkup | |
| 5,023,329 A | * 6/1991 | Neiditch et al. | 536/119 |
| 5,034,551 A | * 7/1991 | Vernon et al. | 556/89 |
| 5,089,608 A | 2/1992 | Walkup | |
| 5,270,071 A | 12/1993 | Sharp | |
| 5,272,137 A | 12/1993 | Blase | |
| 5,298,611 A | 3/1994 | Navia | |
| 5,354,902 A | 10/1994 | Merciadez | |
| 5,374,659 A | 12/1994 | Gowan | |
| 5,384,311 A | 1/1995 | Antenucci | |
| 5,397,588 A | 3/1995 | Antenucci | |
| 5,409,907 A | 4/1995 | Blase | |
| 5,440,026 A | 8/1995 | Khan | |
| 5,470,969 A | * 11/1995 | Sankey et al. | 536/115 |
| 5,498,709 A | 3/1996 | Navia | |
| 5,593,696 A | 1/1997 | McNally | |
| 5,621,005 A | 4/1997 | Gowan | |
| 5,658,919 A | 8/1997 | Ratnaraj | |
| 5,674,522 A | 10/1997 | Shah | |
| 5,817,340 A | 10/1998 | Roche | |
| 5,876,759 A | 3/1999 | Gowan | |
| 5,977,349 A | 11/1999 | Catani | |
| 6,080,481 A | 6/2000 | Ochs | |
| 6,090,401 A | 7/2000 | Gowan | |
| 6,211,246 B1 | 4/2001 | Gelotte | |
| 6,258,381 B1 | 7/2001 | Luber | |
| 6,265,012 B1 | 7/2001 | Shamil | |
| 6,277,409 B1 | 8/2001 | Luber | |
| 6,646,121 B2 | 11/2003 | El Kabbani | |
| 6,809,198 B2 | 10/2004 | El Kabbani | |
| 6,890,581 B2 | 5/2005 | Vernon | |
| 6,939,962 B2 | 9/2005 | Clark | |
| 6,943,248 B2 | 9/2005 | Catani | |
| 6,998,144 B2 | 2/2006 | Merkel | |
| 6,998,480 B2 | 2/2006 | Catani | |
| 7,049,435 B2 | 5/2006 | Catani | |
| 2004/0030124 A1 | 2/2004 | Catani | |
| 2006/0188629 A1 | 8/2006 | Liesen | |
| 2006/0205936 A1 | 9/2006 | Jia | |
| 2006/0276639 A1 | 12/2006 | Fry | |
| 2007/0015916 A1 | 1/2007 | Kabbani | |
| 2007/0100139 A1 | 5/2007 | Fry | |
| 2007/0160732 A1 | 7/2007 | Deshpande | |
| 2007/0227897 A1 | 10/2007 | Li | |
| 2007/0270583 A1 | 11/2007 | Ratnam | |
| 2009/0259034 A1 | 10/2009 | Kerr | |
| 2011/0087018 A1 | 4/2011 | Micinski | |
| 2011/0087019 A1 | 4/2011 | Micinski | |

FOREIGN PATENT DOCUMENTS

| | | |
|---|---|---|
| EP | 0475619 A1 | 3/1992 |
| EP | 0776903 A1 | 6/1997 |
| JP | 2009890 | 1/1990 |
| WO | WO-2010114683 | 10/2010 |

OTHER PUBLICATIONS

Schierbaum et al, Chem. Engg. Technol. 1999, 22(1), 37-41.*

(Continued)

*Primary Examiner* — Ganapathy Krishnan

(74) *Attorney, Agent, or Firm* — RatnerPrestia

(57) ABSTRACT

A method of removing a carboxylic acid from a liquid including a tertiary amide solvent includes: forming an extraction medium including an acid-extracting tin species and an extraction solvent that is immiscible with the tertiary amide solvent; subsequently contacting the liquid with the extraction medium, forming a phase including a de-acidified tertiary amide solvent and a phase including the extraction solvent; and removing the phase including the extraction solvent, to afford a liquid including the de-acidified tertiary amide solvent. The acid-extracting tin species is one or more tin species obtained by reaction of a di(hydrocarbyl) tin oxide with less than one equivalent of a carboxylic acid, or tin species obtainable by reaction of a 1,3-diacyloxy-1,1,3,3-tetra-(hydrocarbyl)distannoxane with an aqueous base. A method of preparing a sucralose-6-acylate includes uses the foregoing method to remove a carboxylic acid from a liquid including a tertiary amide solvent and the sucralose-6-acylate.

51 Claims, 1 Drawing Sheet

(56) References Cited

OTHER PUBLICATIONS

Peruzzo, Valerio, "The Cleavage of Tin-Allyl Bonds in $R_2(CH_2=CH-CH_2)_2Sn$ Substrates as a Route to Organostannoxanes," Journal of Organometallic Chemistry, 66(1974) pp. 437-445.

Schierbaum, Burkhard, "Isolation of Carboxylic Acids from Aqueous Solutions by Extraction with Dialylcarboxlic Amides/Trialkylamines," Chemical Engineering Technology 22(1999) 1, pp. 37-41.

Poole, Loree J., "Regeneration of Carboxylic Acid-Amine Extracts by Back-Extraction with Aqueous Solution of a Volatile Amine," Industrial Engineering Chemistry Research 30(1991), pp. 923-929.

International Search Report and Written Opinion of the International Searching Authority for Application No. PCT/GB/2012/051010 mailed on Aug. 10, 2012.

Combined Search Report and Examination Report for Application GB1110520.2 dated Oct. 7, 2011.

* cited by examiner

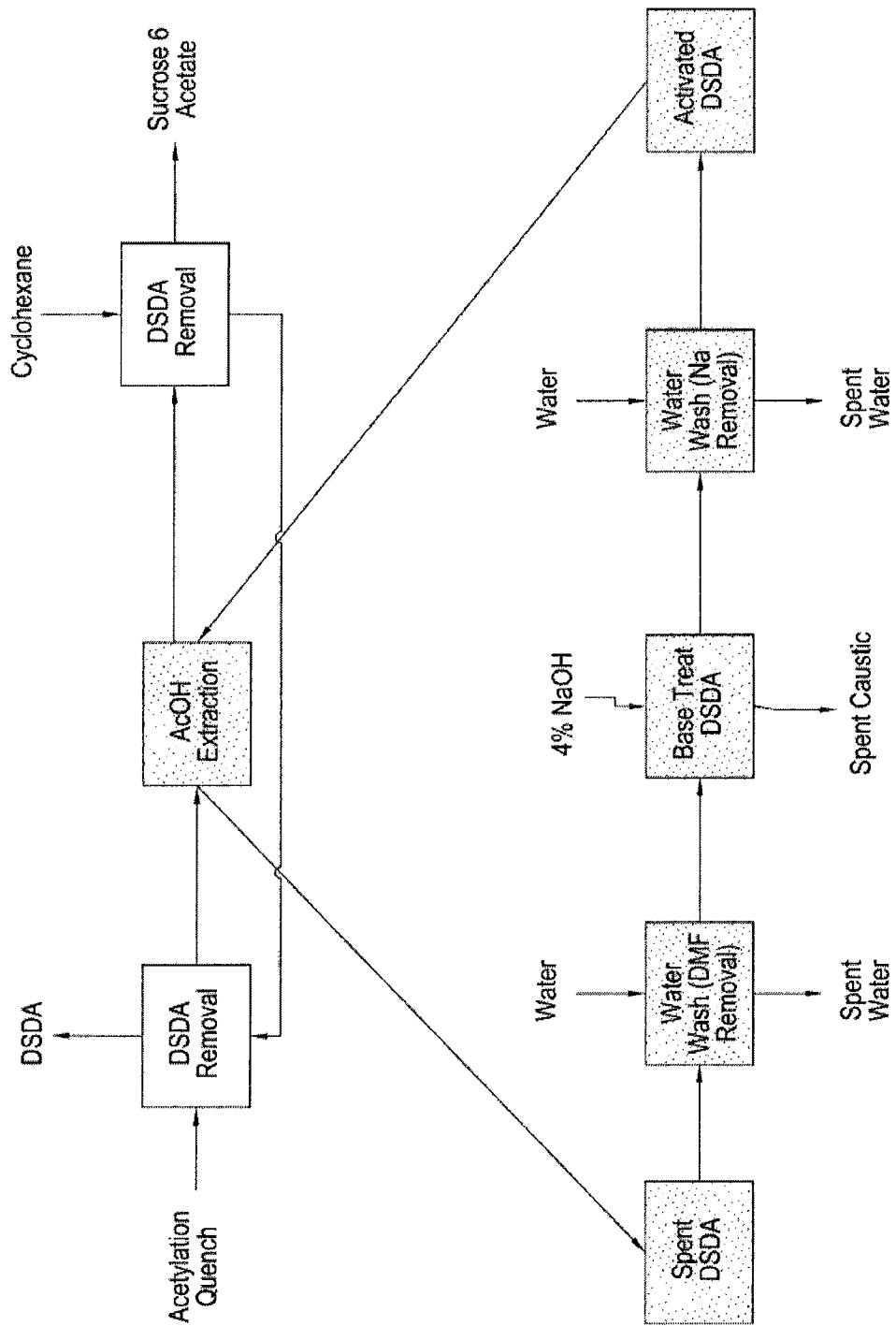

US 8,796,446 B2

EXTRACTION OF CARBOXYLIC ACIDS WITH TIN COMPOUNDS

This application claims priority of U.S. Provisional Patent Application No. 61/484,476, filed 10 May 2011, the entirety of which is incorporated herein by reference.

BACKGROUND OF THE INVENTION

Tertiary amides are used as solvents in a variety of industrial chemical processes, and their recycling for reuse in these processes is of significant commercial value. Depending on the type of reaction performed in the tertiary amide, such recycling may require the removal of reaction byproducts not easily separated from it in a cost-effective manner. One example of such byproducts includes carboxylic acids. In some cases, these must be removed from used solvent as part of recycling, and in other cases they must be removed from the solvent while it is still in use to dissolve process intermediates. The latter situation frequently compounds the difficulty of removing the acids, since potentially sensitive intermediates may be present. The commercial preparation of sucralose is an example of a process where carboxylic acids need to be removed from a tertiary amide solvent, both alone and in the presence of sensitive process intermediates.

Sucralose (4,1',6'-trichloro-4,1',6'-trideoxygalactosucrose), a high-intensity sweetener made from sucrose, can be used in many food and beverage applications.

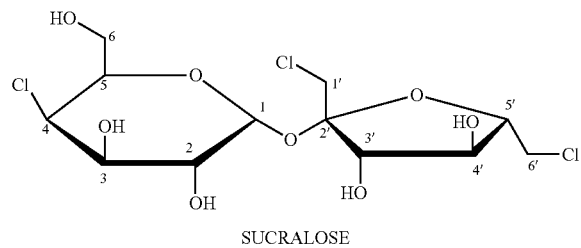

SUCRALOSE

A number of different synthesis routes for the preparation of sucralose have been developed in which the reactive hydroxyl in the 6 position is first blocked with an acyl group to form a sucrose-6-ester. The acyl group is typically acetyl or benzoyl, although others may be used. The sucrose-6-ester is then chlorinated to replace the hydroxyls at the 4, 1' and 6' positions to produce 4,1',6'-trichloro-4,1',6'-trideoxygalactosucrose 6-ester (referred to herein as sucralose-6-ester), followed by hydrolysis to remove the acyl substituent and thereby produce sucralose. Several synthesis routes for formation of the sucrose-6-ester involve tin-mediated acylation reactions, with illustrative examples being disclosed in U.S. Pat. Nos. 4,950,746; 5,023,329; 5,089,608; 5,034,551; and 5,470,969, all of which are incorporated herein by reference.

Various chlorinating agents may be used to chlorinate the sucrose-6-ester, and most commonly a Vilsmeier-type salt such as Arnold's Reagent will be used. One suitable chlorination process is disclosed by Walkup et al. (U.S. Pat. No. 4,980,463), incorporated herein by reference. This process uses a tertiary amide, typically N,N-dimethyl formamide ("DMF"), as the chlorination reaction solvent. After the chlorination is complete, adducts of Arnold's reagent on the base sucrose moiety and excess chlorinating reagent are neutralized ("quenched") with aqueous base to provide the sucralose-6-ester in an aqueous solution, accompanied by the tertiary amide solvent and salts resulting from reactions of the chlorination reagent. The sucralose-6-ester is then deacylated to produce sucralose. One suitable deacylation process is taught by Navia et al, U.S. Pat. No. 5,498,709, the entire disclosure of which is incorporated herein by reference.

In such processes, carboxylic acids need to be removed at various points in the process. Accordingly, facile means of removing these acids are of commercial value.

SUMMARY OF THE INVENTION

In one aspect, the invention provides a method of removing a carboxylic acid from a liquid including a tertiary amide solvent. The method includes the steps of:

contacting the liquid including the tertiary amide solvent with an extraction medium including an acid-extracting tin species and an extraction solvent that is immiscible with the tertiary amide solvent, thereby forming a phase including a de-acidified tertiary amide solvent and a phase including the extraction solvent; and removing the phase including the extraction solvent, to afford a liquid including the de-acidified tertiary amide solvent;

wherein the acid-extracting tin species is selected from the group consisting of tin species obtainable by reaction of a di(hydrocarbyl)tin oxide with less than one equivalent of a carboxylic acid, tin species obtainable by reaction of a 1,3-diacyloxy-1,1,3,3-tetra-(hydrocarbyl)distannoxane with an aqueous base, and combinations of these.

In particular, the method includes the steps of:

A) forming an extraction medium including an acid-extracting tin species and an extraction solvent that is immiscible with the tertiary amide solvent;

B) subsequently contacting the liquid including the tertiary amide solvent with the extraction medium, thereby forming a phase including a de-acidified tertiary amide solvent and a phase including the extraction solvent; and C) removing the phase including the extraction solvent, to afford a liquid including the de-acidified tertiary amide solvent;

wherein the acid-extracting tin species is selected from the group consisting of tin species obtainable by reaction of a di(hydrocarbyl)tin oxide with less than one equivalent of a carboxylic acid, tin species obtainable by reaction of a 1,3-diacyloxy-1,1,3,3-tetra-(hydrocarbyl)distannoxane with an aqueous base, and combinations of these.

The invention also provides a method of preparing a sucrose-6-acylate, including, in order, the steps of:

(i) providing a first reaction mixture including sucrose, a tertiary amide solvent and an organotin-based acylation promoter;

(ii) removing water from the first reaction mixture to afford a second reaction mixture that is substantially free from water;

(iii) adding a carboxylic acid anhydride to the second reaction mixture to afford a third reaction mixture, thereby producing a sucrose-6-acylate; and (iv) removing carboxylic acid from the third reaction mixture by a method according to the present invention.

BRIEF DESCRIPTION OF THE DRAWINGS

FIG. 1 is a schematic diagram of a process for removing acetic acid from a process stream comprising sucrose-6-acetate, according to the invention.

DETAILED DESCRIPTION OF THE INVENTION

The invention provides a method of removing carboxylic acids from tertiary amide streams by reactive extraction of the acids with certain tin compounds. The method is applicable to a variety of situations in which a carboxylic acid needs to be removed. For purposes of example, the present disclosure describes how to use the inventive methods as an aid in the manufacture of sucralose, but the invention is not restricted to acid removal in that narrow context. Indeed, these methods are applicable to any process in which carboxylic acids need to be removed from a tertiary amide solvent.

Nonlimiting examples of tertiary amide solvents from which acids may be removed include N,N-dimethyl formamide (DMF), N,N-diethyl formamide, N,N-dibutyl formamide, N,N-dimethyl acetamide, and N-methyl-2-pyrrolidone. For simplicity, the present invention will be described with respect to the use of DMF as the solvent used for sucralose synthesis, and the solvent from which carboxylic acids are removed by reactive extraction. Nonetheless, the removal of acids from any tertiary amide solvent, with or without the presence of sucralose process intermediates, is within the scope of this invention.

The inventors have found that, during the manufacture of sucralose, significant amounts of lower carboxylic acids may be produced as side products or byproducts during various phases of the synthesis sequence. These typically include acetic acid, in the case where sucrose-6-acetate is used as an intermediate in the process. For simplicity, the discussion hereinafter will refer to the removal of acetic acid. However, other acids may be present in addition or instead, depending on the specific synthesis route used for making the sucralose. For example, formic acid can form by hydrolysis of DMF if that solvent is used in the process, e.g., to form a Vilsmeier-type salt. Other exemplary acids include $C_3$-$C_7$ monocarboxylic acids, for example benzoic acid. The removal of any carboxylic acid from any tertiary amide solvent is contemplated according to the invention.

Unfortunately, carboxylic acids may contribute to the corrosion of manufacturing equipment, and thus, their presence may be problematic. In particular, significant amounts of these acids end up in the tertiary amide solvent that is used and subsequently recovered, purified and recycled in the process. Thus, it is desirable to remove these acids from the tertiary amide solvent.

It is also necessary to remove acetic acid from the process stream containing the carbohydrate (sucrose-6-acetate) since acetic acid will react with and consume significant amounts of the chlorinating agent (Vilsmeier) in the next step of the process. In addition, when acetic acid reacts with the Vilsmeier reagent in the chlorination step, undesirable reaction products are produced which lower the yield of the desired carbohydrate product as well as reducing the efficiency of the DMF recovery process.

However, acetic acid forms a high boiling azeotrope with DMF. This azeotrope boils several degrees higher than the solvent DMF (at atmospheric pressure). As a result, the removal of acetic acid (in DMF) by distillation first requires the removal of the majority of the solvent DMF, followed by continued distillation to remove the higher boiling acetic acid-DMF azeotrope. Consequentially, removal of the majority of the acetic acid requires significantly higher temperatures and lower pressures than would be required for the removal of acetic acid from a solution that does not form a high boiling azeotrope. This distillation effectively removes the vast majority of all of the solvent from the system and results in a very viscous carbohydrate product that has been significantly heat stressed. This heat stress results in significant degradation of the desired carbohydrate and a correspondingly lower yield. The inventors have found that these problems can be mitigated if the amount of acid in the distillation feed is minimized as much as possible so that water can then be removed under distillation conditions that are much milder, leaving the majority of the DMF behind with the sucrose-6-acetate.

The invention provides methods of removing carboxylic acids from a liquid comprising a tertiary amide solvent by extracting the acids with a tin compound, referred to herein as an "acid-extracting" tin compound, dissolved in a solvent that is immiscible with the tertiary amide solvent. As used herein, the term "immiscible" means not miscible, i.e., not capable of being mixed in all proportions. One facile way of producing an acid-extracting tin compound is by deacylating an acylated tin compound. The term "acylated tin compound" means a compound that includes an acyloxy substituent on tin, i.e., a compound having at least one Sn—O-acyl moiety. The deacylation may be achieved by treating the acylated tin compound in a water-immiscible solvent with an aqueous base. The deacylation may be partial or complete with respect to the number of O-acyl groups on a given tin atom, as well as with respect to the mole fraction of tin compounds that has been deacylated, and is preferably done under conditions such that the resulting acid-extracting tin compound remains substantially soluble in the solvent. Preferably, at least 50% of the tin originally present in solution as dissolved acylated tin compounds remains in solution after deacylation.

Typically at least 95%, or preferably 98% of the tin remains in solution, as this eases handling, but the process works effectively even with most or essentially all of the tin in an insoluble form. For example, reaction of a 1,3-diacyloxy-1,1,3,3-tetra-(hydrocarbyl)distannoxane with sufficient aqueous base may form an insoluble di(hydrocarbyl)tin oxide, and this may be used as the acid-extracting tin compound. Additional suitable acid-extracting tin species may in turn be produced by reaction of a di(hydrocarbyl)tin oxide with a carboxylic acid in an amount less than the amount stoichiometrically calculated to convert all of the di(hydrocarbyl)tin oxide to a 1,3-diacyloxy-1,1,3,3-tetra-(hydrocarbyl)distannoxane, which would not be an acid-extracting tin compound according to the invention. Typically, this will mean using less than one equivalent of carboxylic acid per mole of di(hydrocarbyl)tin oxide, and more typically the amount will be less than 0.75 equivalents or less than 0.6 equivalents. The amount will typically be at least 0.1 equivalents per mole, and more typically at least 0.25 equivalents, or at least 0.4 equivalents.

Typically at least 50 mol % of the acylated tin compound is converted to acid-extracting tin compound. More typically at least 75%, or at least 90% is converted. Relatively high levels of conversion naturally improve efficiencies, but in some embodiments the process is fully operable even with very low levels of conversion to acid-extracting tin compounds. Typical water-immiscible solvents suitable for use include hydrocarbons, for example aliphatic, cycloaliphatic, and aromatic hydrocarbons. Specific suitable examples include cyclohexane, n-heptane, toluene, and isooctane (2,2,4-trimethylpentane), although others may be used. It should be noted that the acyl groups on the acylated tin compound need not be the same as the acyl groups of the carboxylic acid that is extracted.

Following is an example describing conversion of an exemplary acylated tin compound, 1,3-diacetoxy-1,1,3,3-tetrabutyldistannoxane (distannoxane diacetate, or DSDA) to an acid-extracting tin compound that is subsequently used to remove acetic acid from DMF. Additional steps relevant to sucralose manufacture are included, to more clearly and completely show one practical embodiment of the invention In an optional preliminary step, dilute DSDA (12% DSDA in cyclohexane) is washed with water to extract DMF that may be present due to previous processing. The ratio of water to DSDA solution may for example be in a range from 0.05 to 0.2 parts of water per part of DSDA solution by volume. The water wash can be conducted in one or more stages, depending on how much DMF needs to be removed, using any equipment suitable for liquid-liquid extraction (liquid-liquid centrifugal extractor, mixer settler, agitated tank and decanting tank, etc.). The heavy phase containing water and DMF is easily separated from the DSDA/cyclohexane phase.

The DSDA is converted to an acid-extracting tin compound by base treatment of the DSDA/cyclohexane phase with dilute aqueous base, typically at 40-75° C. to keep the tin species in solution. However, the tin species need not remain in solution for this reaction to proceed properly. While not wishing to be bound by any particular theory or explanation, the inventors believe that the reaction of base with DSDA replaces one acetate group on the DSDA with a hydroxyl group. For example, the resulting species may be 1-hydroxy-3-acetoxy-1,1,3,3-tetrabutyldistannoxane. Regardless of the exact species, however, the acid-extracting tin compound contains fewer O-acyl groups than does DSDA, yet remains substantially soluble in cyclohexane.

Sodium carbonate, sodium bicarbonate, and sodium hydroxide are exemplary suitable bases, although others may be used instead. Typically the base will be provided as an aqueous solution at a concentration of about 1% to 8% by weight. The amount of base will typically be the stoichiometrically calculated amount needed to replace one acetate group on from 50% to 95% of the DSDA. For example, one mole of DSDA may be treated with from 0.50 to 0.95 mole of NaOH. Adding more base than 0.95% of stoichiometric may convert some of the DSDA to dibutyl tin oxide (DBTO), which is insoluble in cyclohexane, DMF and water. This may be undesirable in some situations if the insoluble material is difficult to handle in the particular equipment being used, but di(hydrocarbyl)tin oxides such as DBTO are nonetheless capable of reactively extracting the carboxylic acid according to the invention. The base treatment may be conducted in any equipment suitable to perform liquid-liquid extraction (liquid-liquid centrifugal extractor, mixer settler, agitated tank and decanting tank, etc.). The heavy phase containing water and the salt from the base treatment (sodium acetate, in this example) is easily separated from the acid-extracting tin compound/cyclohexane phase.

Optionally, the acid-extracting tin compound/cyclohexane phase is washed with water to remove residual sodium salt(s). This may conveniently be done at a temperature from 45-75° C., but other temperatures can be used. A typical ratio of water to DSDA/cyclohexane phase may be between 0.5 and 0.2 by volume. The water extraction may be conducted in any equipment suitable to perform liquid-liquid extraction (liquid-liquid centrifugal extractor, mixer settler, agitated tank and decanting tank, etc.). The heavy phase containing water and sodium salt(s) is easily separated from the acid-extracting tin compound in cyclohexane.

The acid-extracting tin compound is then used to reactively extract acetic acid from a liquid comprising DMF, for example one containing sucrose-6-acetate prepared as an intermediate in a sucralose preparation process. The extraction is conveniently performed at 40-75° C., at which temperatures the majority of the tin species remains soluble. Nonetheless, lower temperatures at which large amounts of tin species become insoluble may still be used according to the invention because these species react well to form soluble species even at the lower temperatures. Typically, the acid-extracting tin compound is used in an amount stoichiometrically equivalent to from 80% to 110% of the acetic acid present in the sucrose-6-acetate/DMF solution, based on the assumption that one mole of acid-extracting tin compound reacts with one mole of acetic acid to produce one mole of DSDA. The reactive extraction can be conducted in any equipment suitable to perform liquid-liquid extraction (liquid-liquid centrifugal extractor, mixer settler, agitated tank and decanting tank, etc.). The heavy phase containing DMF and sucrose-6-acetate, now essentially free of acetic acid, can be easily separated from the cyclohexane phase, which now contains DSDA. The DSDA/cyclohexane phase can be reused by repeating the previous steps (water extraction, base treatment, $2^{nd}$ water extraction) to again form acid-extracting tin compound. Typically, the acid extraction removes more than 50% of the acid in a single extraction and greater than 85% with multiple extractions.

The acid-free solution of sucrose-6-acetate in DMF contains residual DSDA and water which is preferably removed before the chlorination step to form sucralose-6-acetate, the precursor of sucralose. Residual DSDA can be easily removed by liquid-liquid extraction with cyclohexane. The water can be removed by simple distillation/evaporation in any of a variety of equipment types, such as a wiped film evaporator, falling film evaporator, batch evaporator, etc. The sucrose-6-acetate may then be chlorinated and further processed to provide sucralose as described elsewhere herein. The foregoing approach may also be used to remove carboxylic acids from DMF streams not containing process intermediates, prior to using the thus-purified DMF in a process.

A key advantage of the above-described process is that since the acetic acid has been largely removed from the DMF, only water and cyclohexane need to be removed, and this can be done at significantly lower temperatures than would be needed if the high boiling point azeotrope of acetic acid and DMF also needed to be volatilized. In the case where the DMF contains sucralose intermediates, as in this example, the lower temperature reduces carbohydrate decomposition and increases product yield. Similar advantages may be expected for treatment of tertiary amide solvents containing chemical intermediates for other processes.

Reactive extraction of carboxylic acids with acid-extracting tin compounds provides significant advantages over conventional ways of removing the carboxylic acid. Such traditional methods typically involve volatilization at relatively high temperatures, which can be problematic. For example, a typical conventional method uses a thin film evaporator at a process stream temperature in excess of 75° C. in order to strip out the carboxylic acid, and in the case of sucralose manufacture such high temperatures can result in greater than 5% yield loss due to carbohydrate decomposition. Further, in the case where the carboxylic acid is acetic acid, the formation of a water/DMF/acetic acid azeotrope makes it necessary to concentrate the sucrose-6-acetate to more than 80% dry solids in the bottom of the evaporator to remove 80% of the acetic acid. The high concentration often causes plugging due to high viscosity. These problems are largely avoided by using the reactive extraction methods of this invention, which allow removal of carboxylic acids and stripping of water under significantly milder conditions. Sufficient water and cyclohexane is removed by concentrating the sucrose-6-acetate to less than 40% DS. The water can be brought to a low level while leaving the majority of the DMF with the sucrose-6-acetate stream.

Suitable equipment for performing the extractions of this invention includes any known in the chemical engineering art. For example, countercurrent mixer-settler units may be used. Other suitable extraction techniques include batteries of single stage centrifuges or multi-stage centrifuges, such as Robatel BXP series, Podbielniak centrifugal extractors. Also suitable are counter current column technologies such as Scheibel and Karr extraction columns. In some embodiments, simple batch extractions followed by decanting may be used. Packed/sieve tray columns may also be used.

FIG. 1 is a schematic diagram of an exemplary process for removing acetic acid from a process stream comprising sucrose-6-acetate, and more particularly from a quenched process stream following the acetylation of sucrose to form sucrose-6-acetate. According to this example, the quenched process stream results from an acetylation reaction of sucrose using DSDA as an organotin-based acylation promoter, and suitable procedures for carrying out the acetylation reaction are described hereinbelow. The quenched process stream comprises sucrose-6-acetate, DMF, DSDA and acetic acid.

In a first step, the quenched acetylation process stream (referred to as "Acetylation Quench" in FIG. 1) is washed in order to remove organotin-based acylation promoter, in this case DSDA. The extraction solvent of the present invention may suitably be used for this washing step, and cyclohexane is used in the exemplary process of FIG. 1.

Following the washing step, the process stream is contacted with an extraction medium according to the present invention (referred to as "Activated DSDA" in FIG. 1). According to this example, DSDA is reacted with aqueous sodium hydroxide to form an acid-extracting tin species, and the extraction medium comprises this acid-extracting tin species in an extraction solvent, for example cyclohexane. Prior to contacting with the process stream, the extraction medium is washed with water to remove, e.g., sodium salts.

The step of contacting the process stream with the extraction medium is carried out in, for example, a liquid-liquid centrifugal extractor, a mixer settler, an agitated tank, a decanting tank, or any other suitable apparatus for performing liquid-liquid extraction.

The step of contacting the process stream with the extraction medium forms a phase comprising a de-acidified process stream (comprising DMF and sucrose-6-acetate), and a phase comprising the extraction solvent (comprising cyclohexane and DSDA). The phase comprising the extraction solvent (referred to as "Spent DSDA" in FIG. 1) is removed, and the de-acidified process stream is washed in order to remove any residual DSDA. The extraction solvent of the present invention may suitably be used for this washing step, and cyclohexane is used in the exemplary process of FIG. 1. The resulting de-acidified process stream comprising sucrose-6-acetate may then be used as required. For example, the sucrose-6-acetate may be converted to sucralose. Suitable procedures for carrying out this conversion are described hereinbelow.

The phase comprising the extraction solvent removed in the above step (referred to as "Spent DSDA" in FIG. 1) is washed with water to remove DMF. The resulting solution of DSDA in cyclohexane is then treated with aqueous sodium hydroxide to form an extraction medium as already described above, and this extraction medium is then washed and contacted with the process stream as already described above. Thus, according to the exemplary process of FIG. 1, the extraction medium is regenerated and reused in a continuous loop.

Although FIG. 1 illustrates a process according to the present invention by reference to specific reagents and solvents, it will of course be recognized that the illustrated process could also be carried out using other reagents and solvents mentioned herein.

An exemplary overall process for producing sucralose, incorporating acid extraction methods according to the invention, is as follows.

First, the hydroxyl in the 6 position of sucrose is blocked with an ester group, such as acetate or benzoate, using DMF as the reaction solvent. The acetic acid formed during the blocking reaction is removed by reactive extraction with an acid-extracting tin compound according to the invention, and water is removed from the mixture by volatilization. Then the hydroxyls in the 4, 1', and 6' positions of the resulting sucrose-6-ester are converted to chloro groups, with inversion of the stereochemical configuration at the 4 position. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference. Then the ester group in the 6 position of the resulting sucralose-6-ester is removed, and sucralose, the resulting product, is purified and isolated. The process, or any of the individual steps thereof, can be either batch or continuous processes. Following are details of how some embodiments of the process may be performed.

Preparation of Sucrose-6-Ester

Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

A typical preparation of sucrose-6-ester employs a two-step process. First, sucrose is contacted in a solvent with an organotin-based acylation promoter (such as DSDA), and water of reaction is removed to form a tin-sucrose adduct.

The organotin-based acylation promoter is an acylated tin compound, for example a 1,3-diacyloxy-1,1,3,3-tetra-(hydrocarbyl)distannoxane. The term "hydrocarbyl" refers to an alkyl, cycloalkyl, aryl, or aralkyl group. The hydrocarbyl group of the 1,3-diacyloxy-1,1,3,3-tetra-(hydrocarbyl)distannoxane is preferably an alkyl group, more preferably a $C_1$-$C_8$ alkyl group, and most preferably a butyl group, so that 1,1,3,3-tetrabutyldistannoxanes are particularly preferred. It is convenient if the acyloxy group matches that of the carboxylic anhydride to be used, so that, for example, when a sucrose-6-acetate is being prepared, 1,3-diacetoxy-1,1,3,3-tetrabutyldistannoxane (distannoxane diacetate or DSDA) is most preferred.

Preferably 0.5 to 2.5 molar equivalents, more preferably 0.75 to 1.2 molar equivalents, still more preferably 0.9 to 1.1 molar equivalents, and most preferably 1.0 molar equivalents of acylation promoter per mole of sucrose is present in the reaction mixture.

The water removal may be accomplished by any convenient method. For example, an added non-polar co-solvent capable of removing water by co-distillation, such as described in Sankey, U.S. Pat. No. 5,470,969; White, EP 0 776 903; and Vernon, EP 0 475 619, the disclosures of which are incorporated herein by reference, may be used to facilitate efficient removal of the water of reaction. Such solvents are typically ones that do not react with the tertiary amide solvent, the organotin-based acylation promoter, or the sucrose; that produce a mixture with the tertiary amide solvent, the organotin-based acylation promoter, and the sucrose; that reflux with an internal reaction temperature within the range of from about 75° C. to about 153° C., preferably less than 100° C.; that co-distill with water; and that do not render the sucrose insoluble. Such solvents are typically those that are immiscible with water and form a constant-composition minimum-boiling azeotrope with water, such as saturated hydrocarbons, aromatic hydrocarbons, chlorinated hydrocarbons, ketones, and ethers. Examples of such solvents include cyclohexane, n-heptane, toluene, and isooctane (2,2,4-trimethylpentane). Water removal can also be accomplished without the addition of co-solvent, such as described in U.S. patent application Ser. Nos. 12/901,808 and 12/901,820, both filed Oct. 11, 2010.

Then, the reaction mixture containing the tin-sucrose adduct is contacted with a carboxylic acid anhydride, usually in a small stoichiometric excess relative to the sucrose, thereby forming the sucrose-6-ester and carboxylic acid as a byproduct. Typically the mixture is then contacted with water to convert any excess carboxylic anhydride to acid. The organotin acylation promoter and/or its reaction products may then be removed from the reaction mixture, typically by extraction with a hydrocarbon solvent such as cyclohexane, but the remaining solution of the sucrose-6-ester in the DMF contains some amount of water and carboxylic acids that must be removed prior to use in the next step, conversion of the hydroxyls at the 4, 1', and 6'-positions to chloro groups. This may be achieved using the above-described methods of acetic acid extraction with acid-extracting tin compound, followed by water removal via volatilization.

Preparation of Sucralose-6-Ester

To convert sucrose-6-ester to sucralose-6-ester, the hydroxyls at the 4, 1', and 6' positions of the sucrose-6-ester are converted to chloro groups, and the stereochemical configuration at the 4 position is inverted. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference.

The chlorination process comprises the following steps. A reaction mixture is prepared comprising the sucrose-6-ester, a tertiary amide, and at least seven molar equivalents of a chlorination agent. For example, in one process, the sucrose-6-ester can be added in a feed stream that comprises about 20 wt % to about 40 wt % of the sucrose-6-ester. The ratio by weight of tertiary amide to total carbohydrate in the reaction mixture may be about 5:1 to about 12:1. Alternatively, a preformed chloroformiminium salt, such as (chloromethylene)dimethylammonium chloride (Arnold's reagent), can be used. (Chloromethylene)dimethylammonium chloride can be prepared, for example, by the reaction of phosgene with N,N-dimethyl formamide. Typically, the molar ratio of the (chloromethylene)dimethylammonium salt to the sucrose-6-ester is about 7:1 to about 11:1.

Subsequently, the hydroxyl groups of the sucrose-6-ester at the 2, 3, 4, 1', 3', 4', and 6' positions are converted to O-alkylformiminium groups. The resulting reaction mixture is heated at a temperature or temperatures and for a period of time or times sufficient to produce a product containing a derivative of sucralose-6-ester in which the remaining hydroxyl groups remain as O-alkylformiminium groups. For example, Walkup, U.S. Pat. No. 4,980,463, the disclosure of which is incorporated herein by reference, and Fry, U.S. 2007/0100139, the disclosure of which is incorporated herein by reference, disclose such processes.

Because formation of a chloroformiminium salt or Vilsmeier reagent is not essential to the chlorination reaction, the term "chlorination agent" refers to any compound that can be used to form a chloroformiminium salt or Vilsmeier reagent, or that can convert the hydroxyl groups of a sucrose-6-ester to chloro groups. Some chlorination agents that can be reacted with a tertiary amide to form a chloroformiminium salt include, for example, phosgene, phosphorus oxychloride, phosphorus pentachloride, thionyl chloride, sulfuryl chloride, oxalyl chloride, trichloromethyl chloroformate ("diphosgene"), bis(trichloromethyl)carbonate ("triphosgene"), and methanesulfonyl chloride. Tertiary amides that can be used include, for example, N,N-dimethyl formamide (DMF), N-formyl piperidine, N-formyl morpholine, and N,N-diethyl formamide. When N,N-dimethyl formamide is used as the tertiary amide, it can also be used as the reaction solvent. Co-solvents can be used at up to about 80 vol % or more of the liquid phase of the reaction medium. Useful co-solvents are those which are both chemically inert and which provide sufficient solvent power to enable the reaction to become essentially homogeneous at the monochlorination stage, for example toluene, o-xylene, 1,1,2-trichloroethane, 1,2-diethoxyethane, diethylene glycol dimethyl ether.

Quenching the reaction mixture with aqueous base restores the hydroxyl groups at the 2, 3, 3', and 4' positions and forms the sucralose-6-ester. The reaction mixture can be quenched by the addition of about 0.5 to about 2.0 molar equivalents, typically about 1.0 to about 1.5 molar equivalents, of alkali relative to the amount of chlorination agent used in the reaction. An aqueous solution of an alkali metal hydroxide, such as sodium or potassium hydroxide; an aqueous slurry of an alkaline earth metal hydroxide, such as calcium hydroxide; or aqueous ammonium hydroxide can be used to quench the reaction. For example, an aqueous solution of an alkali metal hydroxide, such as aqueous sodium hydroxide, that contains about 5 wt % to about 35 wt %, typically about 8 wt % to about 20 wt %, and preferably about 10 wt % to about 12 wt % can be used.

As described below, quenching can be carried out by adding alkali to the reaction mixture, using either a dual stream process or a circulated process. In each case pH and temperature are controlled during addition of the alkali. Quenching is typically carried out at a pH between about 8.5 to about 10.5 and at a temperature of about 0° C. to about 60° C. Preferably, the pH should not be permitted to rise above about 10.5 during the course of the quenching reaction if deacylation is to be performed in a separate step. However, the pH may be higher (typically below about 12.0) if quenching and deacylation are to be performed in one combined step.

In the dual stream process, quenching is carried out by slow addition of the aqueous alkali with simultaneous slow addition of the chlorination reaction material into a reaction vessel. The chlorination reaction mixture and aqueous alkali are simultaneously added slowly until the desired quantity of chlorination reaction mixture has been added. Further aqueous alkali is added until the desired pH is reached. Then the temperature and pH are maintained at the desired levels for the remainder of the reaction. This process can be a batch or continuous process.

In the circulated process, quenching is carried out by circulating the chlorination reaction mixture from a vessel through a circulation loop. Chlorination reaction mixture and aqueous alkali are added slowly into this circulation loop. Sufficient aqueous alkali is added until the desired pH is reached. Then the temperature and pH are maintained at the desired levels for the remainder of the reaction. This process can be a batch or continuous process. Following quenching, the reaction mixture can optionally be neutralized by the addition of aqueous acid, for example aqueous hydrochloric acid.

The resulting mixture comprises sucralose-6-ester, other carbohydrates including chlorinated carbohydrate impurities, unreacted tertiary amide, and salts in an aqueous solvent in which the predominant solvent is water.

Conversion of Sucralose-6-Ester to Sucralose

The sucralose-6-ester containing aqueous feed stream typically comprises both sucralose and sucralose-6-ester. Methods for hydrolyzing sucralose-6-ester are disclosed, for example in Catani, U.S. Pat. Nos. 5,977,349, 6,943,248, 6,998,480, and 7,049,435; Vernon, U.S. Pat. No. 6,890,581; El Kabbani, U.S. Pat. Nos. 6,809,198, and 6,646,121; Navia, U.S. Pat. Nos. 5,298,611 and 5,498,709, and U.S. Pat. Pub. 2004/0030124; Liesen, U.S. Pat. Pub. 2006/0188629 A1; Fry, U.S. Pat. Pub. 2006/0276639 A1; El Kabbani, U.S. Pat. Pub. 2007/0015916 A1; Deshpande, U.S. Pat. Pub. 2007/0160732 A1; and Ratnam, U.S. Pat. Pub. 2007/0270583 A1; the disclosures of which are all incorporated herein by reference.

For example, (a) sucralose-6-ester can be hydrolyzed to sucralose by raising the pH of the reaction mixture to about 11±1 at a temperature and for a time sufficient to effect removal of the protecting group, and (b) the tertiary amide is removed by, for example, stream stripping. Either step (a) or step (b) can be carried first. Alternatively, conversion of sucralose-6-ester to sucralose can be carried in methanol containing sodium methoxide. A trans-esterification reaction occurs that forms sucralose and the methyl ester of the acid, for example methyl acetate when the sucralose-6-ester is sucralose-6-acetate. The methyl ester of the acid can be removed by distillation, and the resulting sucralose containing product dissolved in water. The sucralose is eventually purified and isolated.

INDUSTRIAL APPLICABILITY

The process of the invention is useful in the preparation of sucralose. Sucralose is a high-intensity sweetener that can be used in many food and beverage applications, as well as in other applications. Such applications include, for example, beverages, combination sweeteners, consumer products, sweetener products, tablet cores (Luber, U.S. Pat. No. 6,277,409), pharmaceutical compositions (Luber, U.S. Pat. No. 6,258,381; Roche, U.S. Pat. No. 5,817,340; and McNally, U.S. Pat. No. 5,593,696), rapidly absorbed liquid compositions (Gelotte, U.S. Pat. No. 6,211,246), stable foam compositions (Gowan, Jr., U.S. Pat. No. 6,090,401), dental floss (Ochs, U.S. Pat. No. 6,080,481), rapidly disintegrating pharmaceutical dosage forms (Gowan, Jr., U.S. Pat. No. 5,876,759), beverage concentrates for medicinal purposes (Shah, U.S. Pat. No. 5,674,522), aqueous pharmaceutical suspensions (Ratnaraj, U.S. Pat. No. 5,658,919; Gowan, Jr. U.S. Pat. Nos. 5,621,005 and 5,374,659; and Blase, U.S. Pat. Nos. 5,409,907 and 5,272,137), fruit spreads (Antenucci, U.S. Pat. No. 5,397,588; and Sharp, U.S. Pat. No. 5,270,071), liquid concentrate compositions (Antenucci, U.S. Pat. No. 5,384,311), and stabilized sorbic acid solutions (Merciadez, U.S. Pat. No. 5,354,902). The determination of an acceptable sweetness can be accomplished by a variety of standard "taste test" protocols known in the art which are well known to those skilled in the art, such as, for example, the protocols referred to in Merkel, U.S. Pat. No. 6,998,144, and Shamil, U.S. Pat. No. 6,265,012.

The advantageous properties of this invention can be observed by reference to the following examples which illustrate but do not limit the invention.

EXAMPLES

The following examples illustrate the removal of acetic acid from a DMF solution containing sucrose-6-acetate as part of a sucralose preparation process.

Example 1

DSDA solution (90.07 g/assay 85% DSDA and 15% cyclohexane) was diluted with cyclohexane (506.06 g) to give a 596 grams of a 12.8% solution of DSDA. This mixture contained about 127.6 mmoles of DSDA. This mixture was treated with 121.02 g of 1N NaOH (about 121 mmoles) or about 0.95 equivalents relative to the DSDA. Water was also added to the mixture (133 g) and the mixture was heated to about 60° C. with stirring. Almost all of the solids remained dissolved at this temperature, with only a small quantity of solids undissolved. The resulting cyclohexane phase contained acid-extracting tin compound.

A sample of sucrose-6-acetate (99.20 g) in DMF containing 3.82% acetic acid (63.2 mmoles) was added to a flask. Next 153.72 grams of the acid-extracting tin compound solution was added at 60° C. to the flask with stirring. This solution contained tin species resulting from deacylation with 31.2 mmole of base (121 mmole×153.72/596), thus providing about 31.2 mmole of acetic acid-extracting capacity. The mixture was stirred for about 5 minutes without heating. The phases were separated, and the sucrose-6-acetate phase was determined to contain 2.31% acetic acid, corresponding to a 40% reduction. It should be noted that performing this step at 60° C. or higher keeps the tin compounds essentially fully dissolved. While this is convenient, it is not necessary to keep the tin compounds dissolved for the reaction to proceed, and after reaction both phases become essentially solids-free regardless of the reaction temperature.

The sucrose-6-acetate phase was treated a second time in a similar matter using 159.7 grams of tin/cyclohexane. This solution contained tin species resulting from deacylation with 32.3 mmoles of base. After this treatment, the sucrose-6-acetate phase contained 0.679% acetic acid, an 82% reduction vs the original 3.82%.

The sucrose-6-acetate phase was treated a third time in a similar matter using 161.1 grams of tin/cyclohexane. This solution contained tin species resulting from deacylation with 32.7 mmoles of base. After this treatment, the sucrose-6-acetate phase contained only 0.0853% acetic acid, a 97.8% reduction vs the original 3.82%.

The assays of the starting material and final product were as follows:

|  | Starting Material | Final Product |
| --- | --- | --- |
| wt % sucrose-6-acetate | 13.21 | 14.95 |
| wt % other carbohydrates | 3.37 | 3.95 |
| wt % acetic acid | 3.82 | 0.0853 |

Example 2

A solution of DSDA in cyclohexane (63.68 g/assay 76.2%) was diluted in cyclohexane (436.72 g) to give a 10% solution of DSDA. This mixture contained about 80.9 mmoles of DSDA. The mixture was treated with 76.34 g of 1N NaOH (about 76.3 mmoles) or about 0.94 equivalents relative to the DSDA. Water was also added to the mixture (100 g) and the mixture was heated to about 60° C. with stirring. The cyclohexane phase now contained acid-extracting tin compound.

A sample of sucrose-6-acetate in DMF (50.24 g) containing 2.75% acetic acid (23.0 mmoles) was added to a flask. Next 124.96 grams of the acid-extracting tin compound solution was added at 62° C. to the flask with stirring. This solution contained tin species resulting from deacylation with 20.2 mmole of base. The mixture was stirred for about 5 minutes without heating. The phases were separated, and the sucrose-6-acetate phase was determined to contain 0.636% acetic acid, a 77% reduction.

The sucrose-6-acetate phase was treated a second time in a similar matter using 104.22 grams of tin/cyclohexane. This solution contained tin species resulting from deacylation with 16.8 mmoles of base. After this treatment, the sucrose-6-acetate phase contained 0.073% acetic acid, a 97.3% reduction vs the original 2.75%.

The assays of the starting material and final product were as follows:

|  | Starting Material | Final Product |
| --- | --- | --- |
| wt % sucrose-6-acetate | 9.16 | 10.58 |
| wt % other carbohydrates | 1.92 | 2.20 |
| wt % acetic acid | 2.75 | 0.073 |

Example 3

Sucrose in dimethylformamide was reacted with DSDA with removal of water, and the resulting mixture was contacted with acetic anhydride to form sucrose-6-acetate. After subsequent addition of water, DSDA was recovered from the mixture via a 2-stage extraction with cyclohexane to yield a 15.6% solution of DSDA, which was then treated as follows.

1. A 1162 g portion of the DSDA solution was diluted with 338 g of cyclohexane to provide 1500 grams of a 12.8% DSDA solution.

2. A 2-liter flask was charged with 1500 grams of diluted DSDA/cyclohexane from step 1 and 300.0 grams of water. The mixture was agitated at ambient temperature for 5 minutes. After removal of the aqueous layer, the water wash was repeated again with another 300 grams of water, resulting in 90+% DMF removal and substantially complete carbohydrate removal.

3. The cyclohexane layer from step 2 was treated with dilute sodium hydroxide as follows. A 1 liter flask was charged with 600 grams of DSDA/cyclohexane layer (containing 0.128 moles DSDA) and 107 grams of 4% sodium hydroxide (0.107 moles) and agitated for 20 minutes at 60° C. After a 20 minutes settling period, the spent sodium hydroxide layer was removed. The cyclohexane layer (now containing an acid-extracting tin compound) was analyzed for % tin, which calculated as the equivalent of 83% of the DSDA molecules having been mono-deacylated.

4. To a 1 L flask was charged 600 grams of step 3 cyclohexane product layer and 120 grams of deionized water. The mixture was agitated for 20 minutes at 60° C. to extract sodium salts, and the resulting aqueous layer was found to contain 170 ppm sodium ions. Step 4 was repeated with another 600 grams of step 3 product and 120 grams of water.

5. To a 1 L flask was charged 362 grams of step 4 product (washed acid-extracting tin compound) and 145 grams of sucrose-6-acetate/DMF solution (containing 2.22% acetic acid and 11.9% total carbohydrates). The mixture was agitated for 20 minutes at 60° C., settled, and the layers were separated. The upper "used" acid-extracting tin compound layer was saved for recycling back to step 1, while 136.2 grams of the lower aqueous/DMF/carbohydrate layer was recharged to the same flask and re-extracted with another 362 grams of step 4 product.

| Before extraction: | |
| --- | --- |
| Total carbohydrate | 11.9% |
| Sucrose-6-acetate | 10.37% |
| DSDA | 1910 ppm |
| Acetic acid | 2.22% |
| After 1$^{st}$ Extraction: | |
| Total Carbohydrate | 12.1% |
| Sucrose-6-acetate | 10.47% |
| DSDA | 895 ppm |
| Acetic acid | 0.61% |
| After 2nd Extraction: | |
| Total Carbohydrate | 13.6% |
| Sucrose-6-acetate | 11.76% |
| DSDA | 922 ppm |
| Acetic acid | 0.33% |

A single extraction reduced the contained acetic acid by 73%. Two extractions reduced the contained acetic acid by 85%.

6. To a 250 mL separatory funnel was charged 94 grams of the lower carbohydrate-containing layer of step 5 and 75 grams cyclohexane. After shaking for 5 minutes at ambient temperatures, the bottom product layer was analyzed as containing 123 ppm DSDA.

Example 4

In this example, acetic acid was extracted from DMF that did not contain carbohydrates.

1. A 625 gram portion of 12% DSDA (125 mmoles) in cyclohexane was heated to 60° C. and mixed with 112.5 grams of 4% sodium hydroxide (112.5 mmoles). The mole ratio of sodium hydroxide to DSDA was 0.9. The mixture was agitated for 15 minutes and allowed to separate and the bottom aqueous layer was discarded.

2. A 195 gram portion of step 1 product (upper layer, containing acid-extracting tin compound) and 100 grams of 15% water/83% DMF/2% acetic acid were mixed and agitated at 60° C. for 15 minutes. The layers were allowed to separate and 92 grams of bottom aqueous DMF layer was removed for a second extraction. The mole ratio of acid-extracting tin compound to acetic acid was 1.1.

3. A 195 gram portion of step 1 product (acid-extracting tin compound layer) and 86 grams of the bottom layer from step #2 were mixed and agitated at 60° C. for 15 minutes. The layers were allowed to separate and 74 grams of bottom layer was removed.

|  | % acetic acid |
| --- | --- |
| Initial aqueous DMF/acetic acid | 1.95 |
| After one extraction | 0.82 |
| After two extractions | 0.31 |

Analysis showed that a single extraction removed 58% of the acetic acid. The second extraction removed 62% of the remaining acid for a total 2-step extraction of 84%.

Example 5

In this example, the acid-extracting tin species was obtained by reaction of dibutyl tin oxide (DBTO) with less than one equivalent of acetic acid. This acid extracting tin species was used to extract acetic acid from DMF that did not contain carbohydrates, analogous to Example 4.

1. Cyclohexane (234.50 g) and glacial acetic acid (19.30 g; 0.321 mol) were first mixed together at 60° C. for 20 minutes before DBTO (100.00 g; 0.402 mol) was added. The mole ratio of acetic acid to DBTO was therefore 0.80. The mixture was left to agitate for 2 hours. Thereafter, 25 ml of water was added and the mixture was stirred for 15 minutes. The mixture was then left to settle for 30 minutes to allow the two layers to separate. The top organic layer was then collected and, the bottom aqueous layer was discarded together with the rag layer.

2. The top organic layer (containing the acid-extracting tin compound and DSDA) was diluted to approximately 12% DSDA concentration before performing acetic acid extraction.

3. An aqueous solution of 15% water, 83% DMF and 2% acetic acid was prepared. The acetic acid extraction was then carried out according to the procedures of Example 4.

4. For the first extraction, 195 g of the diluted organic layer from above step 2 was mixed with 100 g of the aqueous solution from above step 3 at 60° C. for 15 minutes. The two layers were left to settle for a while. 92 g of the bottom aqueous layer was then collected for a second extraction and the top organic layer was discarded.

5. For the second extraction, 195 g of the diluted organic layer from above step 2 was mixed with 86 g of the bottom aqueous layer collected from the first extraction of above step 2 at 60° C. for 15 minutes. The two layers were left to settle for a while. 74 g of the bottom aqueous layer was then collected and the top organic layer was discarded.

The aqueous layers after both the first and second extraction, as well as the initial aqueous solution of above step 3, were analyzed for % acetic acid. The results are shown in the table below:

| Sample | Acetic Acid (% w/w) | Extraction Efficiency (%) | | |
| --- | --- | --- | --- | --- |
|  |  | 1st Extraction | 2nd Extraction | Total Extraction |
| Initial Aqueous Solution | 1.9284 | 29.59 |  | 60.24 |
| 1st Extraction | 1.3577 |  | 43.53 |  |
| 2nd Extraction | 0.7667 |  |  |  |

The above table shows the amount of acetic acid left and the extraction efficiency between each aqueous layer. The amount of acetic acid in the aqueous layer decreases with each extraction. Higher extraction efficiency was also found after each extraction. The first extraction was able to remove about 29.59% of the initial amount of acetic acid, and the second extraction removed about 43.53% of the remaining acetic acid. Overall, about 60.24% of acetic acid was removed when two extractions were performed.

Although the invention is illustrated and described herein with reference to specific embodiments, the invention is not intended to be limited to the details shown. Rather, various modifications may be made in the details within the scope and range of equivalents of the claims without departing from the invention.

The invention claimed is:

1. A method of removing a carboxylic acid from a liquid comprising a tertiary amide solvent, comprising the steps of:
   A) forming an extraction medium comprising an acid-extracting tin species and an extraction solvent that is immiscible with the tertiary amide solvent;
   B) subsequently contacting the liquid comprising the tertiary amide solvent with said extraction medium, thereby forming a phase comprising a de-acidified tertiary amide solvent and a phase comprising the extraction solvent; and
   C) removing the phase comprising the extraction solvent, to afford a liquid comprising the de-acidified tertiary amide solvent;
   wherein said step A) of forming the extraction medium comprises contacting a solution comprising a 1,3-diacyloxy-1,1,3,3-tetra-(hydrocarbyl)distannoxane in the extraction solvent with aqueous base to thereby form an aqueous phase and the extraction medium as a separate phase, and removing the aqueous phase.

2. The method of claim 1, wherein the solution comprising the 1,3-diacyloxy-1,1,3,3-tetra-(hydrocarbyl)distannoxane in the extraction solvent comprises the phase comprising the extraction solvent removed in step C.

3. The method of claim 1, further comprising a step of water-washing the solution comprising the 1,3-diacyloxy-1,1,3,3-tetra-(hydrocarbyl)distannoxane before the step of contacting said solution with the aqueous base.

4. The method of claim 1, further comprising a step of water-washing the extraction medium before said step of contacting the liquid comprising the tertiary amide solvent with said extraction medium.

5. A method of removing a carboxylic acid from a liquid comprising a tertiary amide solvent, comprising the steps of:
   A) forming an extraction medium comprising an acid-extracting tin species and an extraction solvent that is immiscible with the tertiary amide solvent;
   B) subsequently contacting the liquid comprising the tertiary amide solvent with said extraction medium, thereby forming a phase comprising a de-acidified tertiary amide solvent and a phase comprising the extraction solvent; and
   C) removing the phase comprising the extraction solvent, to afford a liquid comprising the de-acidified tertiary amide solvent;
   wherein the acid-extracting tin species is cold species obtained by reaction of a 1,3-diacyloxy-1,1,3,3-tetra-(hydrocarbyl)distannoxane with an aqueous base, wherein less than one equivalent of aqueous base is used per acyloxy group on the diacyloxy-1,1,3,3-tetra-(hydrocarbyl)distannoxane.

6. The method of claim 1, wherein the acid-extracting tin species is a di(hydrocarbyl) tin oxide.

7. The method of claim 1, wherein the 1,3-diacyloxy-1,1, 3,3-tetra-(hydrocarbyl)distannoxane is 1,3-diacetoxy-1,1,3, 3-tetrabutyldistannoxane.

8. The method of claim 1, wherein the 1,3-diacyloxy-1,1, 3,3-tetra-(hydrocarbyl)distannoxane is 1,3-dibenzoyloxy-1, 1,3,3-tetrabutyldistannoxane.

9. The method of claim 1, wherein the tertiary amide solvent is selected from the group consisting of dimethyl formamide, diethyl formamide and dibutyl formamide.

10. The method of claim 1, additionally comprising a step of distilling or evaporating and condensing the tertiary amide solvent.

11. The method of claim 1, additionally comprising a step of washing the liquid comprising a tertiary amide solvent with an additional portion of the extraction solvent prior to step B.

12. The method of claim 1, additionally comprising a step of washing the de-acidified tertiary amide solvent resulting from step C with an additional portion of the extraction solvent to remove residual tin compounds.

13. The method of claim 1, wherein the extraction solvent comprises one or more solvents selected from the group consisting of cyclohexane, n-heptane, toluene, and isooctane (2,2,4-trimethylpentane).

14. The method of claim 1, wherein the carboxylic acid that is removed comprises acetic acid.

15. The method of claim 1, wherein the tertiary amide solvent constitutes 30 to 100 wt % of said liquid comprising a tertiary amide solvent.

16. The method according to claim 1, wherein the method removes more than 50% of the carboxylic acid originally present.

17. The method according to claim 1, wherein steps B and C are repeated.

18. The method according to claim 17, wherein the method removes more than 85% of the carboxylic acid originally present.

19. The method of claim 1, further comprising forming a solution of sucrose in the resulting tertiary amide solvent and subsequently converting the sucrose to sucralose.

20. The method of claim 19, wherein said converting comprises converting the sucrose to a sucrose-6-acylate and subsequently converting the sucrose-6-acylate to sucralose.

21. The method of claim 20, wherein the sucrose-6-acylate is sucrose-6-acetate.

22. The method of claim 1, wherein both the liquid comprising the tertiary amide solvent and the liquid comprising de-acidified tertiary amide solvent further comprise a sucrose-6-acylate.

23. The method of claim 22, further comprising converting the sucrose-6-acylate to sucralose.

24. The method of claim 22, wherein the sucrose-6-acylate is sucrose-6-acetate.

25. A method of preparing a sucrose-6-acylate, comprising, in order, the steps of:
(i) providing a first reaction mixture comprising sucrose, a tertiary amide solvent and an organotin-based acylation promoter;
(ii) removing water from the first reaction mixture to afford a second reaction mixture that is substantially free from water;
(iii) adding a carboxylic acid anhydride to the second reaction mixture to afford a third reaction mixture, thereby producing a sucrose-6-acylate; and
(iv) removing carboxylic acid from the third reaction mixture by a method according to claim 1.

26. The method of claim 25, further comprising converting the sucrose-6-acylate to sucralose.

27. The method of claim 25, wherein the sucrose-6-acylate is sucrose-6-acetate.

28. The method of claim 5, wherein the solution comprising the 1,3-diacyloxy-1,1,3,3-tetra-(hydrocarbyl)distannoxane in the extraction solvent comprises the phase comprising the extraction solvent removed in step C.

29. The method of claim 5, further comprising a step of water-washing the solution comprising the 1,3-diacyloxy-1, 1,3,3-tetra-(hydrocarbyl)distannoxane before the step of contacting said solution with the aqueous base.

30. The method of claim 5, further comprising a step of water-washing the extraction medium before said step of contacting the liquid comprising the tertiary amide solvent with said extraction medium.

31. The method of claim 5, wherein the 1,3-diacyloxy-1, 1,3,3-tetra-(hydrocarbyl)distannoxane is 1,3-diacetoxy-1,1, 3,3-tetrabutyldistannoxane.

32. The method of claim 5, wherein the 1,3-diacyloxy-1, 1,3,3-tetra-(hydrocarbyl)distannoxane is 1,3-dibenzoyloxy-1,1,3,3-tetrabutyldistannoxane.

33. The method of claim 5, wherein the tertiary amide solvent is selected from the group consisting of dimethyl formamide, diethyl formamide and dibutyl formamide.

34. The method of claim 5, additionally comprising a step of distilling or evaporating and condensing the tertiary amide solvent.

35. The method of claim 5, additionally comprising a step of washing the liquid comprising a tertiary amide solvent with an additional portion of the extraction solvent prior to step B.

36. The method of claim 5, additionally comprising a step of washing the de-acidified tertiary amide solvent resulting from step C with an additional portion of the extraction solvent to remove residual tin compounds.

37. The method of claim 5, wherein the extraction solvent comprises one or more solvents selected from the group consisting of cyclohexane, n-heptane, toluene, and isooctane (2,2,4-trimethylpentane).

38. The method of claim 5, wherein the carboxylic acid that is removed comprises acetic acid.

39. The method of claim 5, wherein the tertiary amide solvent constitutes 30 to 100 wt % of said liquid comprising a tertiary amide solvent.

40. The method according to claim 5, wherein the method removes more than 50% of the carboxylic acid originally present.

41. The method according to claim 5, wherein steps B and C are repeated.

42. The method according to claim 41, wherein the method removes more than 85% of the carboxylic acid originally present.

43. The method of claim 5, further comprising forming a solution of sucrose in the resulting tertiary amide solvent and subsequently converting the sucrose to sucralose.

44. The method of claim 43, wherein said converting comprises converting the sucrose to a sucrose-6-acylate and subsequently converting the sucrose-6-acylate to sucralose.

45. The method of claim 44, wherein the sucrose-6-acylate is sucrose-6-acetate.

46. The method of claim 5, wherein both the liquid comprising the tertiary amide solvent and the liquid comprising de-acidified tertiary amide solvent further comprise a sucrose-6-acylate.

47. The method of claim 46, further comprising converting the sucrose-6-acylate to sucralose.

48. The method of claim 46, wherein the sucrose-6-acylate is sucrose-6-acetate.

49. A method of preparing a sucrose-6-acylate, comprising, in order, the steps of:
  (i) providing a first reaction mixture comprising sucrose, a tertiary amide solvent and an organotin-based acylation promoter;
  (ii) removing water from the first reaction mixture to afford a second reaction mixture that is substantially free from water;
  (iii) adding a carboxylic acid anhydride to the second reaction mixture to afford a third reaction mixture, thereby producing a sucrose-6-acylate; and
  (iv) removing carboxylic acid from the third reaction mixture by a method according to claim 5.

50. The method of claim 49, further comprising converting the sucrose-6-acylate to sucralose.

51. The method of claim 49, wherein the sucrose-6-acylate is sucrose-6-acetate.

* * * * *

UNITED STATES PATENT AND TRADEMARK OFFICE
CERTIFICATE OF CORRECTION

| | | |
|---|---|---|
| PATENT NO. | : 8,796,446 B2 | Page 1 of 1 |
| APPLICATION NO. | : 13/463332 | |
| DATED | : August 5, 2014 | |
| INVENTOR(S) | : David T. Coleman et al. | |

It is certified that error appears in the above-identified patent and that said Letters Patent is hereby corrected as shown below:

In the Claims:

At Column 16, line 60, "wherein the acid-extracting tin species is cold species" should read --wherein the acid-extracting tin species is--

Signed and Sealed this
Fourteenth Day of October, 2014

Michelle K. Lee
*Deputy Director of the United States Patent and Trademark Office*